United States Patent
Bennett

(10) Patent No.: US 9,296,320 B2
(45) Date of Patent: Mar. 29, 2016

(54) SEAT SUSPENSION LOCKING APPARATUS

(71) Applicant: Paul Bennett, Powell, OH (US)

(72) Inventor: Paul Bennett, Powell, OH (US)

(73) Assignee: CVG MANAGEMENT CORPORATION, New Albany, OH (US)

( * ) Notice: Subject to any disclaimer, the term of this patent is extended or adjusted under 35 U.S.C. 154(b) by 95 days.

(21) Appl. No.: 14/202,548

(22) Filed: Mar. 10, 2014

(65) Prior Publication Data

US 2014/0265419 A1 Sep. 18, 2014

Related U.S. Application Data

(60) Provisional application No. 61/787,239, filed on Mar. 15, 2013.

(51) Int. Cl.
| | | |
|---|---|---|
| *B60N 2/02* | (2006.01) | |
| *B60N 2/50* | (2006.01) | |
| *B60N 2/44* | (2006.01) | |
| *H04R 1/02* | (2006.01) | |
| *A61B 5/0205* | (2006.01) | |
| *A61B 5/145* | (2006.01) | |
| *A61B 5/18* | (2006.01) | |
| *A61B 5/00* | (2006.01) | |

(52) U.S. Cl.
CPC .............. *B60N 2/502* (2013.01); *A61B 5/0205* (2013.01); *A61B 5/14546* (2013.01); *A61B 5/18* (2013.01); *A61B 5/6893* (2013.01); *A61B 5/742* (2013.01); *A61B 5/746* (2013.01); *A61B 5/7475* (2013.01); *B60N 2/02* (2013.01); *B60N 2/44* (2013.01); *B60N 2/442* (2013.01); *B60N 2/505* (2013.01); *H04R 1/028* (2013.01); *B60N 2205/20* (2013.01); *Y10T 29/49826* (2015.01); *Y10T 403/591* (2015.01)

(58) Field of Classification Search
CPC .... A61B 5/0205; A61B 5/14546; A61B 5/18; A61B 5/6893; A61B 5/742; A61B 5/746; A61B 5/7475; B60N 2/02; B60N 2/44; B60N 2/442; B60N 2/502; B60N 2/505; H04R 1/028
See application file for complete search history.

(56) References Cited

U.S. PATENT DOCUMENTS

| | | | | |
|---|---|---|---|---|
| 3,599,232 | A * | 8/1971 | Tabor | 248/567 |
| 3,861,637 | A * | 1/1975 | DeLongchamp | 248/576 |
| 3,917,209 | A * | 11/1975 | Adams | 248/567 |
| 4,566,667 | A * | 1/1986 | Yanagisawa | 248/561 |
| 5,388,801 | A * | 2/1995 | Edrich et al. | 248/564 |
| 5,538,115 | A * | 7/1996 | Koch | 188/266.6 |
| 5,671,964 | A * | 9/1997 | DeRees et al. | 296/65.02 |
| 6,082,715 | A * | 7/2000 | Vandermolen | 267/131 |
| 2004/0051023 | A1 * | 3/2004 | Bryngelson et al. | 248/550 |
| 2012/0091772 | A1 * | 4/2012 | Egan | B60N 2/0232 297/344.13 |

* cited by examiner

*Primary Examiner* — Glenn Dayoan
*Assistant Examiner* — Paul Chenevert
(74) *Attorney, Agent, or Firm* — Kegler Brown Hill & Ritter Co., L.P.A.; James Pingor

(57) ABSTRACT

A locking apparatus for a seat assembly for a vehicle is provides and includes a latching component attached to one of a stationary part or a movable part of a seat assembly, a receiving component disposed on the other of the stationary part or the movable part of a seat assembly, wherein the latching component engages the receiving component, and an activation component that activates the latching component. Upon activation of the locking device, the latching component engages the receiving component thereby locking the movable part to the stationary part in a collapsed state thereby reducing vibrational noise caused by the movable part during operation of the vehicle.

17 Claims, 6 Drawing Sheets

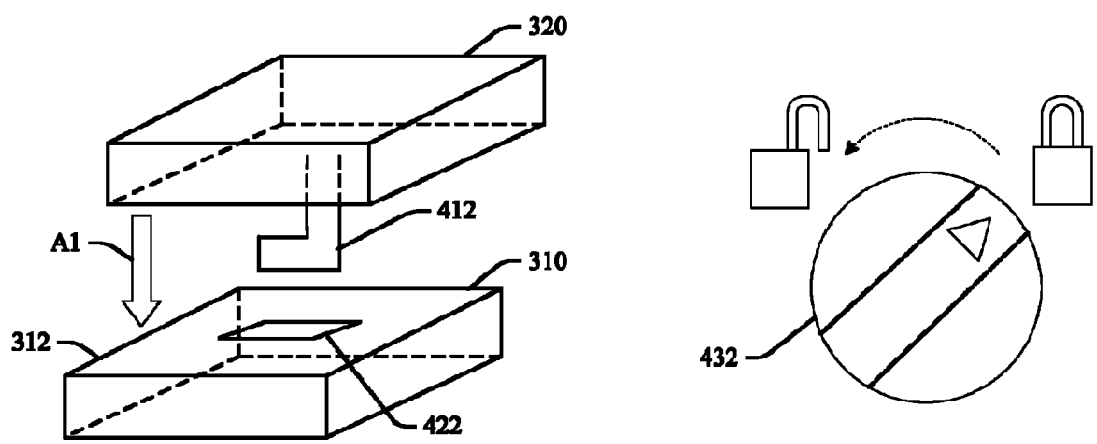
FIG. 4E
FIG. 4F
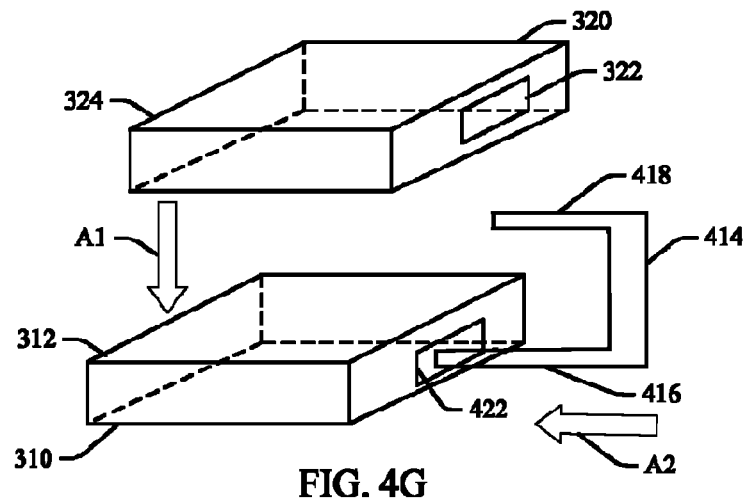
FIG. 4G

SEAT SUSPENSION LOCKING APPARATUS

CROSS-REFERENCE TO RELATED APPLICATIONS

This application claims the benefit of U.S. Provisional Patent application Ser. No. 61/787,239 entitled "SEATING APPARATUS SYSTEMS" filed on Mar. 15, 2013.

ORIGIN

The innovation disclosed herein relates to a vehicle seat and more specifically, to a vehicle seat adjustment indicator.

BACKGROUND

It is well-known to provide a vehicle seat, in particular in a long-haul or heavy goods vehicle, where a seat base is mounted to a floor of the vehicle and a movable seat part is mounted on the seat base. A suspension (e.g., spring, air, gas, etc.) is provided between the seat base and the movable part to isolate some of the vibration experienced by the vehicle cab and hence the seat base from the movable seat part. The driver adjusts or moves the movable seat part, which moves in both a vertical (up/down) and horizontal (fore/aft) direction with respect to the seat base, to achieve a desired seating position.

During operation of the vehicle, however, when a seat (e.g., passenger seat) is unoccupied, the movable seat part vibrates thereby causing unwanted noise for the driver of the vehicle. In a pneumatic system, the air from the system can be exhausted thereby lowering the movable seat part onto the seat base in an attempt to reduce the vibration noise. This, however, results in metal-to-metal wear, as there is no cushioning mechanism between the seat base and the movable seat part, thereby inducing premature wear.

SUMMARY

The following presents a simplified summary in order to provide a basic understanding of some aspects of the innovation. This summary is not an extensive overview of the innovation. It is not intended to identify key/critical elements or to delineate the scope of the innovation. Its sole purpose is to present some concepts of the innovation in a simplified form as a prelude to the more detailed description that is presented later.

In an aspect of the innovation, a seat assembly locking device is disclosed that overcomes the disadvantages mentioned above. The seat assembly locking device locks a movable seat part to a seat base to thereby reduce the vibration caused by the seat assembly during operation of a vehicle.

In another aspect of the innovation, a locking apparatus for a seat assembly for a vehicle is disclosed that includes a latching component attached to one of a stationary part or a movable part of a seat assembly, a receiving component disposed on the other of the stationary part or the movable part of a seat assembly, wherein the latching component engages the receiving component, and an activation component that activates the latching component, wherein upon activation of the locking device, the latching component engages the receiving component thereby locking the movable part to the stationary part in a collapsed state thereby reducing vibrational noise caused by the movable part during operation of the vehicle.

In yet another aspect of the innovation, a seat assembly for a vehicle is disclosed and includes a stationary part attached to a floor of the vehicle, a movable part attached to the stationary part and movable with respect to the stationary part, a suspension assembly movably connecting the movable part to the stationary part, and a locking apparatus that locks the movable part to the stationary part in a collapsed state thereby reducing vibration caused by the movable part during operation of the vehicle.

In still yet another aspect of the innovation, a method of reducing vibration and noise in a seat assembly for a vehicle is disclosed and includes providing a latching component, a receiving component that receives the latching component, and an activation device that activates the latching component, activating the activation device, moving a movable part of the seat assembly toward a stationary part of the seat assembly, engaging the latching component with the receiving component, locking the movable part to the stationary part, and reducing vibrational noise of the movable part during operation of the vehicle.

To accomplish the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

FIG. 4E is an example embodiment illustration of a latching component in accordance with an aspect of the innovation FIG. 4F is an example embodiment illustration of an activation component in accordance with an aspect of the innovation FIG. 4G is an example embodiment illustration of a receiving component in accordance with an aspect of the innovation.

DETAILED DESCRIPTION

Figure 1:
FIG. 1 is a perspective view of a vehicle seat assembly incorporating an innovative seat suspension locking apparatus in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

While specific characteristics are described herein (e.g., thickness), it is to be understood that the features, functions and benefits of the innovation can employ characteristics that vary from those described herein. These alternatives are to be included within the scope of the innovation and claims appended hereto.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Vehicle seat assemblies in, for example, long-haul trucks, includes independent suspensions systems (e.g., mechanical, pneumatic) and are adjustable in a vertical (up/down) and horizontal (fore/aft) direction, such that occupants of the vehicle can adjust the seat in a desired seating position. When a seat (e.g. passenger seats is unoccupied, however, the seat assembly can vibrate during operation of the vehicle, thereby causing unwanted noise inside the cab of the vehicle. In a pneumatic suspension system, air can be exhausted from the system in an attempt to reduce the vibrational noise. This, however, oftentimes results in a metal-to-metal contact, which may damage the seat assembly as the seat still vibrates. The innovation disclosed herein addresses this issue by incorporating a seat assembly locking device that locks the unoccupied seat assembly to reduce the vibration of the seat assembly thereby reducing unwanted noise caused by vehicle vibrations.

With reference now to the figures, FIG. 1 is a perspective illustration of an example seat assembly 100 for a vehicle incorporating a seat suspension locking apparatus in accordance with an aspect of the innovation. The seat assembly 100 includes an occupant seat 110 that attaches to a base unit 120, which is mounted to a floor of the vehicle. It is to be understood that the innovative seat suspension locking apparatus may be incorporated on any type of seat assembly having an independent suspension for any type of vehicle. Thus, the innovative seat suspension locking apparatus is not limited to long-haul trucks.

Figure 2:
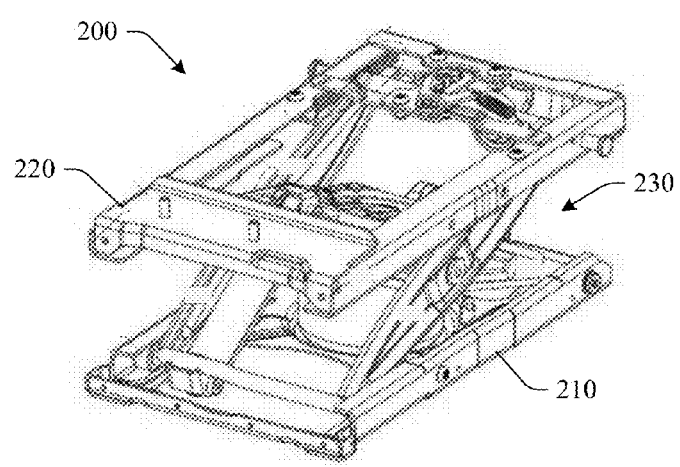
FIG. 2 is a perspective view of a seat suspension assembly incorporating the innovative seat suspension locking apparatus in accordance with an aspect of the innovation.

FIG. 2 is a perspective view of an example base unit 200 in accordance with an aspect of the innovation. The base unit 200 includes a stationary part (lower seat frame) 210 attached to a floor of the vehicle, a movable part (upper seat frame) 220 that moves in multiple directions (e.g., vertical, horizontal, tilt forward and rearward at an angle, etc.) with respect to the stationary part 210, and a suspension assembly 230 that connects the movable part 220 to the stationary part 210. The suspension assembly 200 illustrated in FIG. 2 is a mechanical scissor type suspension system. It is to be understood, however, that the innovative seat assembly locking device may be incorporated on any type of suspension assembly, such as but not limited to a pneumatic or hydraulic suspension assembly. Thus, the suspension assembly illustrated in FIG. 2 is for illustrative purposes only and is not intended to limit the scope of the innovation.

Figure 3:
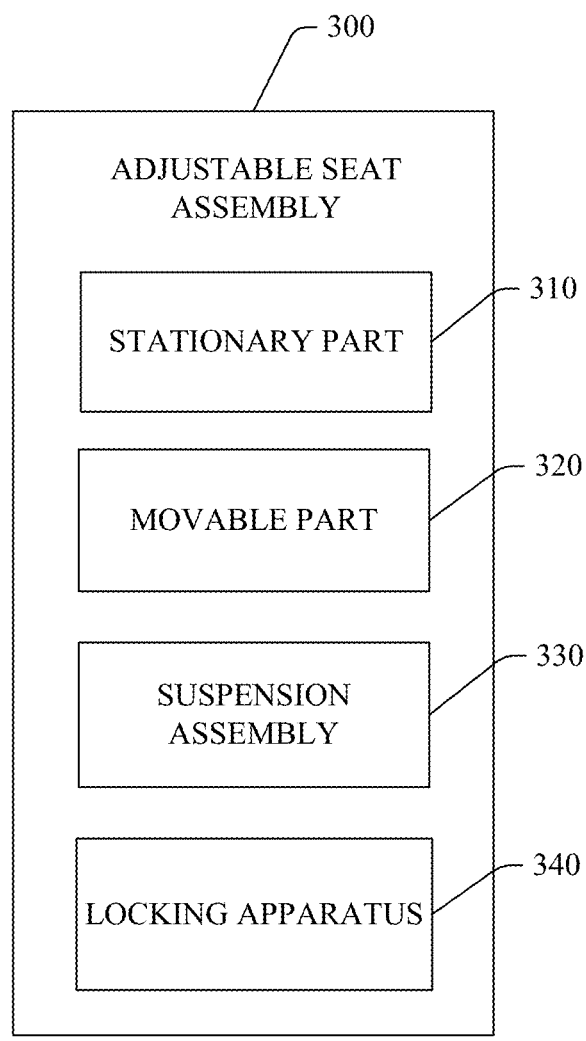
FIG. 3 is a block diagrams illustrating an example embodiment of components of the vehicle seat assembly in accordance with an aspect of the innovation.

FIG. 3 is a block diagram illustration of an example seat assembly 300 that includes the aforementioned stationary part 310, the movable part 320, and the suspension assembly 330. The seat assembly 300 further includes the innovative seat suspension locking apparatus 340 (hereinafter "locking apparatus"). The locking apparatus 300 is configured to provide a means to lock the movable part 304 with the stationary part 302 to reduce the vibration generated by the seat assembly 300 during operation of the vehicle.

Figure 4:
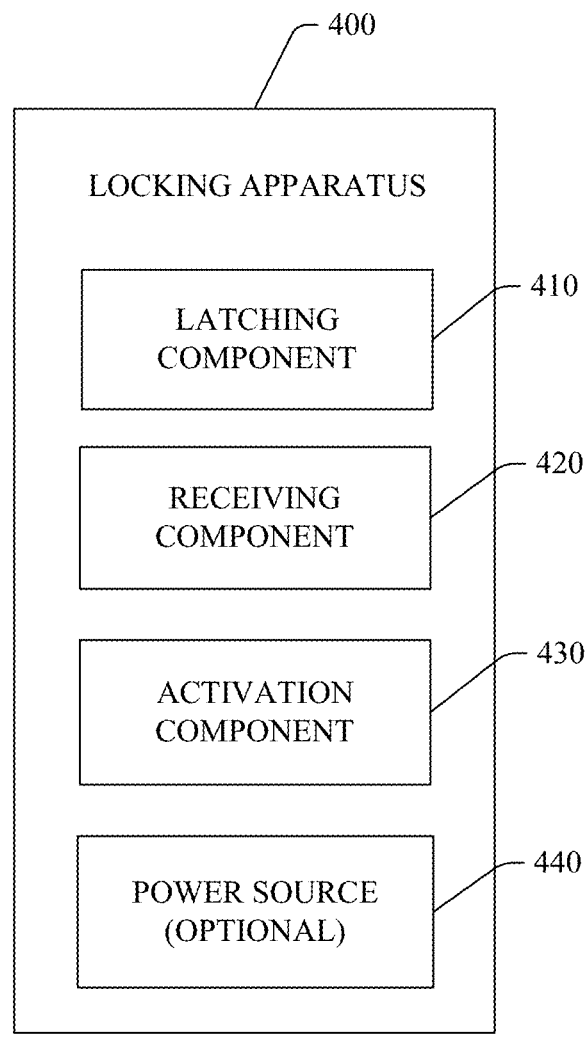
FIG. 4 is a block diagram illustrating an example embodiment of components of the seat suspension locking apparatus in accordance with an aspect of the innovation.

FIG. 4 is a block diagram illustration of an example locking apparatus 400 in accordance with an aspect of the innovation. The locking apparatus 400 includes a latching component 410, a receiving component 420, an activation component 430, and an optional power source 440. As will be described below, in one example embodiment, the locking apparatus 400 is a manual device that is mechanically actuated. In another embodiment, the locking apparatus 400 is an automated device that may be mechanically or electronically actuated.

Figure 4A:
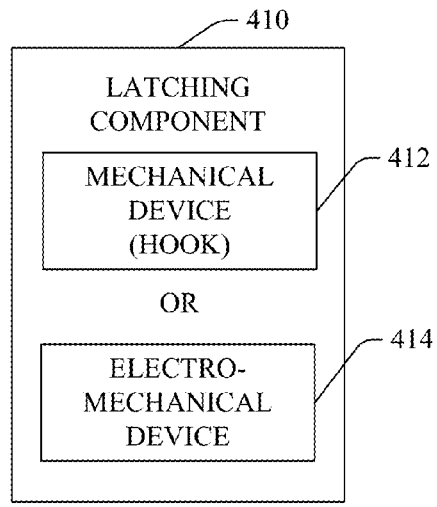
FIG. 4A is a block diagram illustrating an example embodiment of components of a latching component in accordance with an aspect of the innovation.

Referring to FIG. 4A, in one example embodiment, the latching component 410 may be a mechanical device 412, such as but not limited to, a J-hook, L-hook (FIG. 4E), T-hook, U-shaped latch (FIG. 4G), etc. The latching component 410 may be attached to either the stationary part 310 or the movable part 320 of the seat assembly 300. In another embodiment, the latching component 410 may be an electromechanical device 414, such as but not limited to, a solenoid. It is to be understood, that the latching component 410 may be any type of mechanical or electro-mechanical device and is not limited to the example embodiments disclosed herein.

Figure 4B:
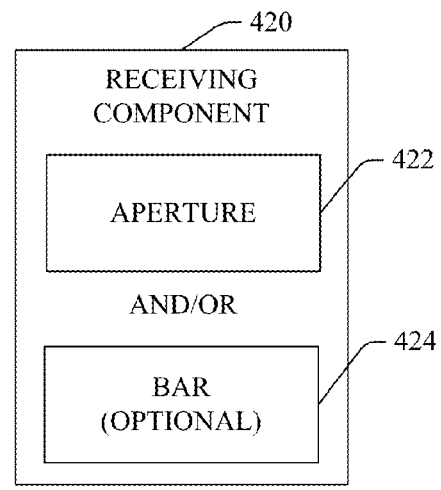
FIG. 4B is a block diagram illustrating an example embodiment of components of a receiving component in accordance with an aspect of the innovation.

Referring to FIG. 4B, the receiving component 420 can be an aperture 422 defined in the stationary part 310 if the latching component 410 is attached to the movable part 320 or defined in the movable part 320 if the latching component 410 is attached to the stationary part 310 of the seat assembly 300. The aperture 422 is configured to receive the latching component 410 when the latching component 410 is actuated. In one aspect, the aperture 422 may include a bar or rod attached near an opening of the aperture to allow the hook to engage. In another example embodiment, the receiving component may be a bar or rod attached to the either the stationary or movable part 310, 320. In another example embodiment, the receiving component may be a plate having an aperture attached to the either the stationary or movable part 310, 320, where the slot receives the latching component 410. Thus, it is to be understood, that the receiving component 420 may be any type of mechanical or electro-mechanical device and is not limited to the example embodiments disclosed herein.

Figure 4C:
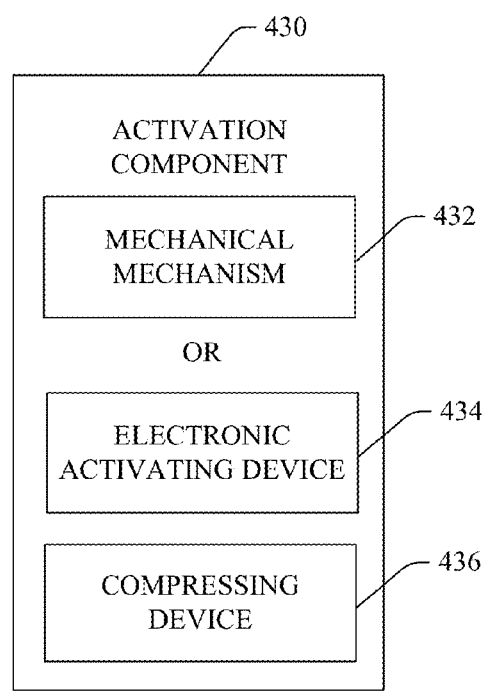
FIG. 4C is a block diagram illustrating an example embodiment of components of an activation component in accordance with an aspect of the innovation.

Referring to FIG. 4C, as will be illustrated further below, the activation component 430 may include a manually operated mechanical mechanism 432 (e.g., rotatable knob, button, toggle, switch, etc.) that is located on either the stationary part 310 or the movable part 320. In another example embodiment, the activation component 430 may be an electronic activating device 434 (e.g., phone, PDA, electronic transmitter, etc.) that may be located inside the vehicle or may be remote. In another embodiment, the activation component 430 may include a compressing device 436 that automatically compresses or collapses the seat assembly 300 upon actuation of the activation component 430.

An example, L-hook 412 latching component 410 is illustrated in FIG. 4E. In this example embodiment, the latching component 410 is attached to the movable part 320 and the receiving component 420 (aperture 422) is defined in the stationary part 310. As mentioned above, the latching component 410 can be attached to the stationary part 310 and the receiving component 420 (aperture 422) can be defined in the movable part 320.

Still referring to FIG. 4E, as the movable part 320 of the seat assembly 300 collapses toward the stationary part 310, as indicated by the arrow A1, the L-hook 412 enters the aperture 422. The L-hook 412 is then rotated by the activation component 430, similar to the example mechanical mechanism 432 shown in FIG. 4F. When the movable part 320 is released, the suspension assembly 330 biases the movable part 320 away from the stationary part 310. The L-hook 412, however, engages a frame portion 312 of the stationary part 310 to lock the movable part 320 in the collapsed position. To release the movable part 320 from the collapsed position, the activation component 430 is rotated in the opposite direction to disengage the L-hook 412 from the frame portion 312 of the stationary part 310. It is to be understood, that the activation component 430 is not limited to a rotational device, as shown in FIG. 4F. Rather, the activation device can be a knob, a button, a switch, a handle, etc. that when activated rotates, pivots or slides the latching component 410 to engage the receiving component 420.

An example U-shaped latch 414 is illustrated in FIG. 4G. In this example embodiment, the latching component 410 (U-shaped latch 414) is a slidable device that is attached to the stationary part 310 via a lower leg 416 that slides into an aperture 424 defined in a side of the frame portion 312. As the movable part 320 of the seat assembly 300 moves toward the stationary part 310, as indicated by the arrow A1, the U-shaped latch 414 is slid toward the stationary part 310 and the movable part 320, as indicated by the arrow A2. In this regard, an upper leg 418 of the U-shaped latch 414 enters an aperture 322 defined in a side of a frame portion 324 of the movable part 320.

When the movable part 320 is released, the suspension assembly 330 biases the movable part 320 away from the stationary part 310. The lower and upper legs 416, 418, of the U-shaped latch 414, however, engage the frame portions 312, 324 of the stationary part 310 and the movable part 320 respectively to lock the movable part 320 in the collapsed position. To release the movable part 320 from the collapsed position, the U-shaped latch 414 is slid in the opposite direction to disengage the upper leg 416 from the aperture 322 defined in the movable part 320, thereby releasing the movable part 320 from the stationary part 310.

As mentioned above, in another embodiment, the latching component 410 may be an electro-mechanical device 414, such as but not limited to, a solenoid and the activation component 430 may be an electronic activating device 434 (e.g., phone, PDA, electronic transmitter, etc.) that may be located inside the vehicle or may be remote. In addition, the activation component 430 may include a compressing device 436 that automatically compresses or collapses the seat assembly 300 upon actuation of the activation component 430.

Figure 4D:
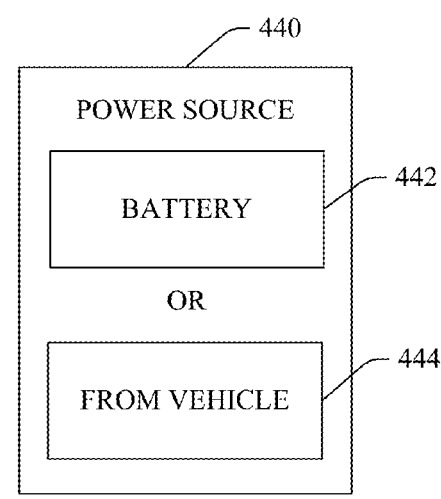
FIG. 4D is a block diagram illustrating an example embodiment of components of a power source in accordance with an aspect of the innovation.

In this embodiment, the suspension assembly 330 may be a pneumatic or hydraulic suspension where upon actuation of the electronic activating device 434, the compressing device 436 automatically compresses the seat assembly 300 by exhausting pneumatic or hydraulic cylinder(s) of the suspension assembly 330. When the seat assembly is fully collapsed, the electro-mechanical device 414, which is attached to either the stationary part 310 or the movable part 320, automatically actuates such that a movable latching mechanism engages an aperture defined in either movable part 320 or the stationary part 310. The compressing device 436 and the electro-mechanical device 414 are powered by the power source 440, which may include a battery 442 or may be vehicle supplied 444, see FIG. 4D.

Figure 5:
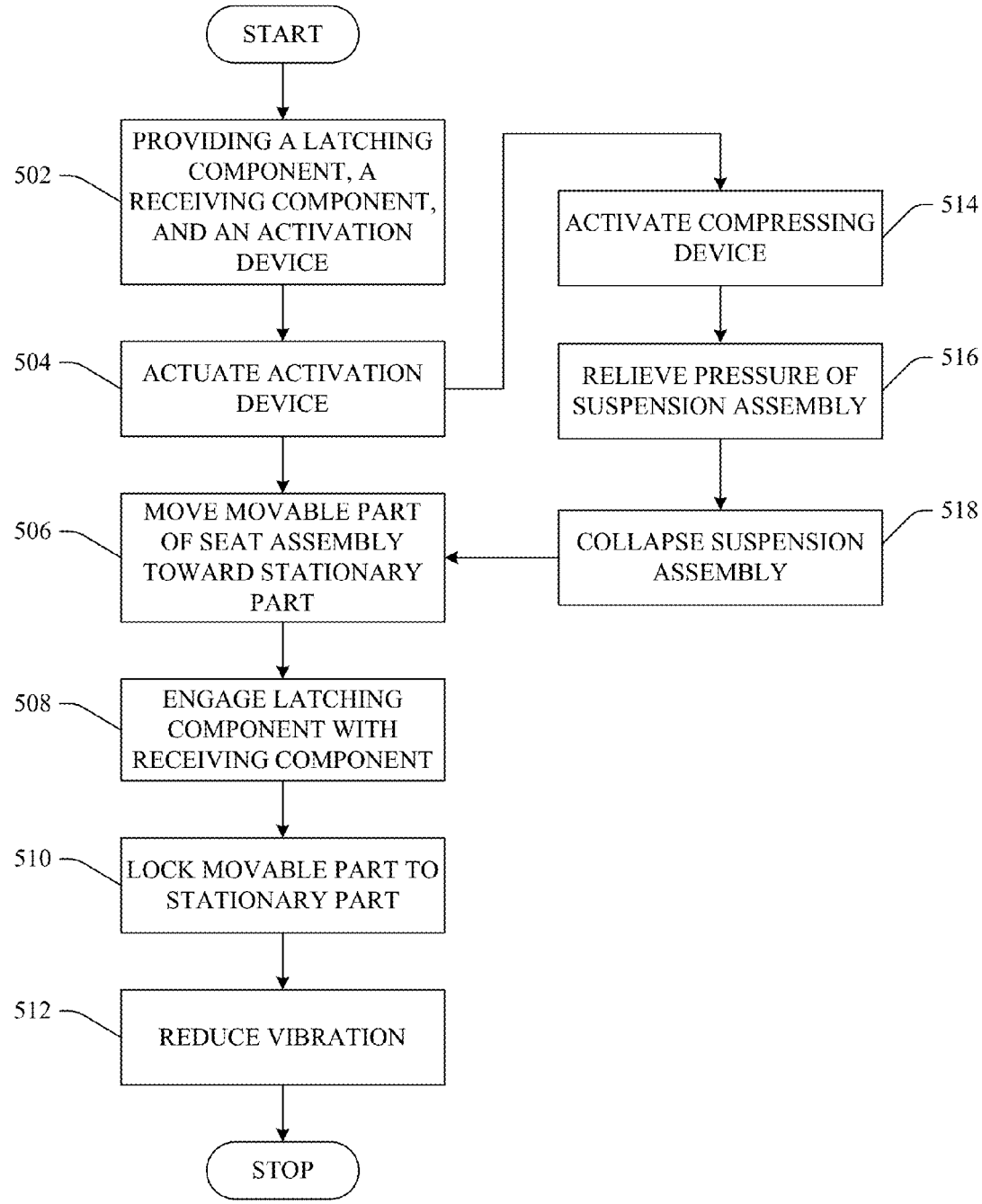
FIG. 5 is a flow chart illustrating a method of reducing vibration and noise in a seat assembly in accordance with an aspect of the innovation.

Referring to FIG. 5, a method 500 of reducing vibration and noise in a seat assembly 300 for a vehicle is illustrated. At 502, the latching component 410, the receiving component 420 that receives the latching component, and the activation device 430 that activates the latching component 410 are provided. At 504, the activation device 430 is actuated and at 506, the movable part 320 of the seat assembly 300 moves toward the stationary part 310 of the seat assembly 300. At 508, the latching component 410 engages the receiving component 420 and at 510, the movable part 320 is locked to the stationary part 310 thereby at 512, reducing vibrational noise of the movable part 320 during operation of the vehicle.

In a modified embodiment, activation of the activation device 430 at 504 includes, at 514 activation of a compressing device 436, at 516, relieving a pressure of the suspension assembly 330 that connects the stationary part 310 and the movable part 320 of the seat assembly 300, and at 518 collapsing suspension assembly 300.

It is to be understood, that the innovation disclosed herein has many applications and is not limited long-haul or heavy goods vehicles. More specifically, the innovation may be applied to any vehicle having an adjustable seat assembly. For example, the innovation may be applied to transport trucks, lighter duty trucks, box trucks, flatbed trucks, sprinter trucks, pick-up trucks, vans, busses, RVs, agriculture equipment (e.g., tractors, excavators, etc.), etc.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A locking apparatus for a seat assembly for a vehicle comprising:
    a latching component attached to one of a stationary part or a movable part of a seat assembly;
    a receiving component disposed on the other of the stationary part or the movable part of a seat assembly, wherein the latching component engages the receiving component; and
    an activation component that activates the latching component,
    wherein upon activation of the locking device, the latching component engages the receiving component thereby locking the movable part to the stationary part in a collapsed state thereby reducing vibrational noise caused by the movable part during operation of the vehicle, and
    wherein the latching component is an electro-mechanical device having a movable latching mechanism that when actuated latches the movable part to the stationary part in a collapsed state thereby reducing vibrational noise caused by the movable part during operation of the vehicle.

2. The locking apparatus of claim 1, wherein the latching component includes one of an L-hook and a U-shaped latch.

3. The locking apparatus of claim 1, wherein the receiving component is an aperture defined in the other of the stationary part or the movable part and is configured to receive the latching component.

4. The locking apparatus of claim 1, wherein the activation component is one of a knob, button, switch that when activated rotates, pivots or slides the latch component to engage the receiving component.

5. The locking apparatus of claim 1, wherein the receiving component is an aperture configured to receive the movable latching mechanism.

6. The locking apparatus of claim 1, wherein the activation component includes an activating device, a compressing device that contracts a suspension assembly of the seat assembly connecting the movable part to the stationary part, such that the movable part moves toward the stationary part, and a power source that powers the compressing device.

7. The locking apparatus of claim 6, wherein the activating device activates the compressing device and may be attached to the seat assembly, attached inside the vehicle or may be an electronic remote device.

8. The locking apparatus of claim 6, wherein the compressing device automatically relieves the pressure of a pneumatic or hydraulic suspension assembly, such that the suspension assembly moves toward the stationary part.

9. A seat assembly for a vehicle comprising:
a stationary part attached to a floor of the vehicle;
a movable part attached to the stationary part and movable with respect to the stationary part;
a suspension assembly movably connecting the movable part to the stationary part; and
a locking apparatus that locks the movable part to the stationary part in a collapsed state thereby reducing vibration caused by the movable part during operation of the vehicle,
wherein the locking apparatus includes an electro-mechanical latching component attached to one of the stationary part and movable part, the electro-mechanical latching component having a movable latching mechanism that when actuated latches the movable part to the stationary part in the collapsed state thereby reducing vibrational noise caused by the movable part during operation of the vehicle.

10. The seat assembly of claim 9, wherein the locking apparatus includes a receiving component defined in the other of the stationary part and the movable part and comprised of an aperture configured to receive the movable latching mechanism.

11. The seat assembly of claim 9, wherein the locking apparatus includes an activating device, a compressing device that contracts a suspension assembly of the seat assembly connecting the movable part to the stationary part, such that the movable part moves toward the stationary part, and a power source that powers the compressing device.

12. The seat assembly of claim 11, wherein the activating device activates the compressing device and may be attached to the seat assembly, attached inside the vehicle or may be an electronic remote device.

13. The seat assembly of claim 11, wherein upon activation of the activating device, the compressing device automatically relieves the pressure of a pneumatic or hydraulic suspension assembly, such that the suspension assembly collapses toward the stationary part.

14. A method of reducing vibration and noise in a seat assembly for a vehicle comprising:
providing a latching component, a receiving component that receives the latching component, and an activation device that activates the latching component;
activating the activation device;
moving a movable part of the seat assembly toward a stationary part of the seat assembly;
engaging the latching component with the receiving component;
locking the movable part to the stationary part; and
reducing vibrational noise of the movable part during operation of the vehicle,
wherein the latching component is an electro-mechanical device having a movable latching mechanism.

15. The method of claim 14, wherein activating the activation device includes:
activating a compressing device;
relieving a pressure of a suspension assembly that connects the stationary part and the movable part of the seat assembly; and
collapsing the pneumatic or hydraulic suspension assembly.

16. The method of claim 15, wherein the suspension assembly is a pneumatic suspension assembly.

17. The method of claim 15, wherein the suspension assembly is a hydraulic suspension assembly.

* * * * *